United States Patent
Wagner et al.

(10) Patent No.: US 10,231,947 B2
(45) Date of Patent: Mar. 19, 2019

(54) ISOCHROMAN COMPOUNDS AND METHODS OF USE THEREOF

(71) Applicant: ARIZONA BOARD OF REGENTS ON BEHALF OF ARIZONA STATE UNIVERSITY, Scottsdale, AZ (US)

(72) Inventors: Carl E. Wagner, Glendale, AZ (US); Pamela A. Marshall, Peoria, AZ (US); Peter W. Jurutka, Scottsdale, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 15/878,289

(22) Filed: Jan. 23, 2018

(65) Prior Publication Data

US 2018/0207125 A1    Jul. 26, 2018

Related U.S. Application Data

(60) Provisional application No. 62/449,495, filed on Jan. 23, 2017.

(51) Int. Cl.
| | |
|---|---|
| A61P 25/28 | (2006.01) |
| A61P 35/00 | (2006.01) |
| A61K 31/352 | (2006.01) |
| C07D 213/36 | (2006.01) |
| C07D 239/42 | (2006.01) |
| C07D 241/18 | (2006.01) |
| C07D 311/74 | (2006.01) |

(52) U.S. Cl.
CPC ............ *A61K 31/352* (2013.01); *A61P 25/28* (2018.01); *A61P 35/00* (2018.01); *C07D 311/74* (2013.01); *C07D 213/36* (2013.01); *C07D 239/42* (2013.01); *C07D 241/18* (2013.01)

(58) Field of Classification Search
CPC ......... A61P 25/28; A61P 35/00; C07D 311/74
USPC ........................................................ 514/249
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,762,844 A | 8/1988 | Grohe et al. |
| 4,820,508 A | 4/1989 | Wortzman |
| 4,826,984 A | 5/1989 | Berlin et al. |
| 4,938,949 A | 7/1990 | Borch et al. |
| 4,980,509 A | 12/1990 | Maignan |
| 4,992,478 A | 2/1991 | Geria |
| 5,006,550 A | 4/1991 | Chandraratna |
| 5,414,156 A | 5/1995 | Cho et al. |
| 5,587,367 A | 12/1996 | Reuchert |
| 5,672,710 A | 9/1997 | Beard et al. |
| 5,780,676 A | 7/1998 | Boehm et al. |
| 5,962,731 A | 10/1999 | Boehm et al. |
| 5,981,776 A | 11/1999 | Diaz et al. |
| 6,137,002 A | 10/2000 | Fisher |
| 6,162,815 A | 12/2000 | Bernardon |
| 6,172,112 B1 | 1/2001 | Brouillette et al. |
| 6,258,775 B1 | 7/2001 | Bernardon et al. |
| 6,291,677 B1 | 9/2001 | Vasudevan |
| 6,303,785 B1 | 10/2001 | Vasudevan |
| 6,313,107 B1 | 11/2001 | Vasudevan |
| 6,545,049 B1 | 4/2003 | Canan-Koch et al. |
| 6,586,460 B1* | 7/2003 | Berlin ................. C07D 311/58 514/432 |
| 6,596,758 B1 | 7/2003 | Brunet et al. |
| 7,655,699 B1 | 2/2010 | Boehm |
| 8,101,662 B2 | 1/2012 | Chandraratna |
| 8,389,538 B2 | 3/2013 | Kakuta et al. |
| 8,460,576 B2 | 6/2013 | Kurisawa et al. |
| 8,475,775 B1 | 7/2013 | Brouillette |
| 9,174,917 B2* | 11/2015 | Wagner ................. C07C 63/66 |
| 9,193,672 B2 | 11/2015 | Yu |
| 9,573,906 B2* | 2/2017 | Wagner ............... C07D 239/28 |
| 9,596,758 B2 | 3/2017 | Tatsuta |
| 9,908,856 B2* | 3/2018 | Wagner ............... C07D 249/18 |
| 10,005,741 B2 | 6/2018 | Wagner et al. |
| 2003/0008273 A1 | 1/2003 | Perlmann et al. |
| 2003/0135053 A1 | 7/2003 | Bernardon |
| 2005/0038098 A1* | 2/2005 | Tachdjian ............ C07D 277/34 514/406 |
| 2006/0106072 A1 | 5/2006 | Boehm et al. |
| 2007/0129392 A1 | 6/2007 | Hong et al. |
| 2007/0185055 A1 | 8/2007 | Jiang et al. |
| 2010/0010084 A1 | 1/2010 | Yu |
| 2010/0029689 A1 | 2/2010 | Hopper |
| 2010/0105728 A1 | 4/2010 | Lagu |
| 2010/0120742 A1 | 5/2010 | Kakuta et al. |
| 2010/0144821 A1 | 6/2010 | Carter et al. |

(Continued)

FOREIGN PATENT DOCUMENTS

| | | |
|---|---|---|
| EP | 0637297 B1 | 8/2000 |
| EP | 1180520 A1 | 2/2002 |

(Continued)

OTHER PUBLICATIONS

Love; J Clin Pathol 2006, 59, 1151-1159. (Year: 2006).*

(Continued)

*Primary Examiner* — Daniel R Carcanague
(74) *Attorney, Agent, or Firm* — Viksnins Harris Padys Malen LLP

(57) ABSTRACT

The invention provides compounds of formula I:

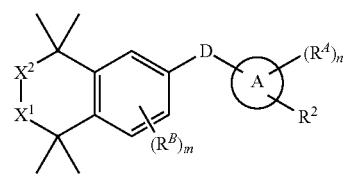

and salts thereof, as well as pharmaceutical compositions comprising such compounds. The compounds are useful for treating cancers, Alzheimer's disease, and conditions associated with demyelination.

8 Claims, No Drawings

(56) References Cited

U.S. PATENT DOCUMENTS

| | | | |
|---|---|---|---|
| 2011/0253936 A1 | 10/2011 | Kurisawa et al. | |
| 2012/0309833 A1* | 12/2012 | Wagner | C07C 63/66 514/569 |
| 2014/0343079 A1* | 11/2014 | Wagner | C07D 239/28 514/256 |
| 2016/0263189 A1 | 9/2016 | Burstein | |
| 2016/0338981 A1* | 11/2016 | Marshall | A61K 31/192 |
| 2017/0008859 A1* | 1/2017 | Wagner | A61K 31/505 |
| 2017/0182046 A1* | 6/2017 | Wagner | A61K 31/505 |
| 2018/0065936 A1 | 3/2018 | Wagner et al. | |
| 2018/0072697 A1 | 3/2018 | Wagner et al. | |
| 2018/0141921 A1 | 5/2018 | Wagner et al. | |
| 2018/0207125 A1* | 7/2018 | Wagner | A61K 31/352 |
| 2018/0207126 A1* | 7/2018 | Wagner | A61K 31/352 |
| 2018/0207156 A1* | 7/2018 | Wagner | A61K 31/505 |

FOREIGN PATENT DOCUMENTS

| | | | | |
|---|---|---|---|---|
| JP | 11-503472 A | 3/1999 | | |
| JP | H111343263 A | 12/1999 | | |
| JP | 2001522350 A | 11/2001 | | |
| JP | 2002515025 A | 5/2002 | | |
| JP | 2010111588 A | 5/2010 | | |
| JP | 2013052386 A | 3/2013 | | |
| JP | 2014076953 A | 5/2014 | | |
| JP | 5784045 B2 | 10/2017 | | |
| WO | 1993021146 A1 | 10/1993 | | |
| WO | 1994015902 A1 | 7/1994 | | |
| WO | WO-9807716 A2 * | 2/1998 | | C07C 69/94 |
| WO | 1998045242 A1 | 10/1998 | | |
| WO | 1999051562 A1 | 10/1999 | | |
| WO | 1999056740 A1 | 11/1999 | | |
| WO | 2000064260 A1 | 11/2000 | | |
| WO | 2002018361 A2 | 3/2002 | | |
| WO | 2002049632 A1 | 6/2002 | | |
| WO | 2002086062 A3 | 10/2002 | | |
| WO | 2004058762 A1 | 7/2004 | | |
| WO | 2004093809 A2 | 11/2004 | | |
| WO | 2005058803 A1 | 12/2004 | | |
| WO | 2005000233 A2 | 1/2005 | | |
| WO | 2005011573 A2 | 2/2005 | | |
| WO | 2005013949 A2 | 2/2005 | | |
| WO | 2005058301 A1 | 6/2005 | | |
| WO | 2005058798 A2 | 6/2005 | | |
| WO | 2006036394 A2 | 4/2006 | | |
| WO | 2007022437 A2 | 2/2007 | | |
| WO | 2007063681 A1 | 6/2007 | | |
| WO | 2008025965 A2 | 3/2008 | | |
| WO | 2008105386 A1 | 9/2008 | | |
| WO | 2010096264 A2 | 8/2010 | | |
| WO | 2011006157 A2 | 1/2011 | | |
| WO | 2011062017 A1 | 5/2011 | | |
| WO | 2011103321 A1 | 8/2011 | | |
| WO | 2013040227 A2 | 3/2013 | | |
| WO | 201356232 A2 | 4/2013 | | |
| WO | 2015109318 A2 | 7/2015 | | |
| WO | 2015130973 A1 | 9/2015 | | |
| WO | 2016140979 A1 | 9/2016 | | |

OTHER PUBLICATIONS

Zacheis; J. Med. Chem. 1999, 42, 4434-4445. (Year: 1999).*
Boehm; J. Med. Chem. 1995, 38, 3146-3155. (Year: 1995).*
Fujii; Bioorganic & Medicinal Chemistry Letters 2010, 20, 5139-5142. (Year: 2010).*
Nadeem; World J Neurol 2015, 5, 5-16. (Year: 2015).*
Santin; J. Med. Chem. 2009, 52, 3150-3158. (Year: 2009).*
Brown; J. Med. Chem. 2004, 47, 1008-1017. (Year: 2004).*
Spruce; J. Med. Chem. 1991, 34, 430-439. (Year: 1991).*
Spruce; J. Med. Chem. 1987 30, 8, 1474-1482. (Year: 1987).*
Liu, et al., "IRX4204 in combination with erlotinib to target distinct pathways in lung cancer cells", J Clin Oncol 35(15 suppl), abstract e14095 (2017), http://ascopubs.org/doi/abs/10.1200/JCO.2017.35.15_suppl.e14095 (downloaded Aug. 3, 2018).
Love, et al., "The structural basis for the specificity of retinoid-X receptor-selective agonists: new insights into the role of helix H12", J. Biol. Chem. 277(13), 11385-11391 (2002).
Lubet, et al., "Chemopreventive efficacy of Targretin in rodent models of urinary bladder, colon/intestine, head and neck and mammary cancers", Oncol Rep 27(5), 1400-1406 (2012).
Luettich, et al., "Systems toxicology approaches enable mechanistic comparison of spontaneous and cigarette smoke-related lung tumor development in the A/J mouse model", Interdiscip Toxicol 7(2), 73-84 (2014).
Mangelsdorf, et al., "A direct repeat in the cellular retinol-binding protein type II gene confers differential regulation by RXR and RAR", Cell 66, 555-561 (1991).
Mangelsdorf, et al., "The RXR heterodimers and orphan receptors", Cell 83, 841-850 (1995).
Marshall, et al., "Analysis of differential secondary effects of novel rexinoids: select rexinoid X receptor ligands demonstrate differentiated side effect profiles", Pharma Res Per 3(2), e00122 (2015).
Marshall, "Using *Saccharomyces cerevisiae* to Test the Mutagenicity of Household Compounds: An Open Ended Hypothesis-Driven Teaching Lab", CBE-LSE 6, 307-315 (2007).
McFarland, et al., "Low Dose Bexarotene Treatment Rescues Dopamine Neurons and Restores Behavioral Function in Models of Parkinson's Disease", ACS Chemical Neuroscience 4(11), 1430-1438 (2013).
McFarland, "Pimavanserin, a 5-HT2A inverse agonist, reverses psychosis-like behaviors in a rodent model of Parkinson's disease", Behav. Pharmacol. 22, 681-692 (2011).
Michellys, et al., "Design and Synthesis of Novel RXR-Selective Modulators with Improved Pharmacological Profile.", Bioorg Med Chem Lett 13, 4070-4075 (2003).
Michellys, "Design, synthesis and structure-activity relationship of novel RXR-selective modulators.", Bioorg Med Chem Lett 14, 1593-1598 (2004).
Michellys, et al., "Design, synthesis, and structure-activity relationship studies of novel 6,7-locked-[7-(2-alkoxy-3,5-dialkylbenzene)-3-methylocta]-2,4,6-trienoic acids.", J Med Chem 46, 4087-4103 (2003).
Michellys, et al., "Novel (2E,4E,6Z)-7-(2-alkoxy-3,5-dialkylbenzene)-3-methylocta-2,4,6-trienoic acid retinoid X receptor modulators are active in models of type 2 diabetes.", J Med Chem 46, 2683-2696 (2003).
Miller, et al., "Initial clinical trial of a selective retinoid X receptor ligand, LGD1069", J. Clin. Oncol. 15, 790-795 (1997).
Morishita, et al., "Retinoid X Receptor Ligands with Anti-Type 2 Diabetic Activity", https://www.ncbi.nlm.nih.gov/pubmed/27320332 (2017).
Morris, et al., "AutoDock4 and AutoDockTools4: Automated Docking with Selective Receptor Flexibility", J. Comput. Chem. 30(16), 2785-2791 (2009).
Mortelmens, et al., "The Ames *Salmonella*/microsome mutagenicity assay", Mutat Res 455(1-2), 29-60 (2000).
Muccio, et al., "Conformationally Defined Retinoic Acid Analogues. 4. Potential New Agents for Acute Promyelocytic and Juvenile Myelomonocytic Leukemias", Journal of Medicinal Chemistry 41(10), 1679-1687 (1998).
Mukherjee, et al., "Sensitization of diabetic and obese mice to insulin by retinoid X receptor agonists", Nature 386, 407-410 (1997).
Murthy, et al., "LXR/RXR activation enhances basolateral efflux of cholesterol in CaCo-2 cells", J. Lipid Res. 43, 1054-1064 (2002).
Nahoum, et al., "Modulators of the structural dynamics of the retinoid X receptor to reveal receptor function.", Proc Natl Acad Sci 104, 17323-17328 (2007).
Nakatsuka, et al., "RXR antagonism induces G0/G1 cell cycle arrest and ameliorates obesity by up-regulating the p53-p21Cip1 pathway in adipocytes", The Journal of Pathology 226, 784-795 (2012).
Nakayama, et al., "Discovery of a Potent Retinoid X Receptor Antagonist Structurally Closely Related to RXR Agonist NEt-3IB", ACS Med Chem Lett 2(12), 896-900 (2011).
Natrajan, et al., "Retinoid X receptor activation reverses age-related deficiencies in myelin debris phagocytosis and remyelination", Brain 138 (Pt 12), 3581-3597 (2015).

(56) References Cited

OTHER PUBLICATIONS

Nunez, et al., "Retinoid X receptor alpha controls innate inflammatory responses through the up-regulation of chemokine expression", Proc Natl Acad Sci USA 107(23), 10626-10631 (2010).
O'Boyle, et al., "Open Babel: An open chemical toolbox", J. Cheminf. 3(33), 14 pages (2011).
Ohsawa, et al., "Mechanismof Retinoid X Receptor Partial Agonistic Action of 1-(3,5,5,8,8-Pentamethyl-5,6,7,8-tetrahydro-2-naphthyl)-1H-benzotriazole-5-carboxylic Acid and Structural DevelopmentTo Increase Potency", J. Med. Chem. 56, 1865-1877 (2013).
Ohta, et al., "Diphenylamine-based retinoid antagonists: regulation of RAR and RXR function depending on the N-substituent", Bioorganic & Medicinal Chemistry 19, 2501-2507 (2011).
Ohta, et al., "Potent Retinoid Synergists with a Diphenylamine Skeleton", Biological & Pharmaceutical Bulletin 21(5), 544-546 (1998).
Okayama University, "Synthesis of novel homeostasis modulators by "Westernized Kampo Medicine"—Retinoid X Receptor Partial-Agonists Exert Anti-type 2 Diabetes Effects with Less Adverse Effects than Full-Agonists—", Okayama University eBulletin 7, pp. 20-21 (Jun. 2014).
Olefsky, "Nuclear Receptor Minireview Series", J. Biol. Chem. 276(40), 36863-36864 (2001).
Ordentlich, et al., "Identification of the antineoplastic agent 6-mercaptopurine as anactivator of the orphan nuclear hormone receptor Nurr1", J. Biol. Chem. 278(27), 24791-24799 (2003).
Pangborn, et al., "Safe and Convenient Procedure for Solvent Purification", Organometallics 15, 1518-1520 (1996).
Parry, et al., "A Boronated Benzamide as Melanoma-Seeking Agent.", Bioorg Med Chem Lett 7(3), 361-364 (1997).
Perlmann, et al., "A novel pathway for vitamin a signaling mediated by RXR heterodimerization with NGFI-B and NURR1", Genes & Dev. 9, 769-782 (1995).
Perlmann, "Retinoid Metabolism: a balancing act", Nature Genetics 31, 7-8 (2002).
Prado-Garcia, et al., "Tumor-induced CD8+ T-cell dysfunction in lung cancer patients", Clin Dev Immunol 2012, Article ID 741741, 11 pages, doi: 10.1155/2012/741741 (2012).
Prince, et al., "Bexarotene capsules and gel for previously treated patients with cutaneous T-cell lymphoma: Results of the Australian patients treated on phase II trials.", Australasian Journal of Dermatology 42, 91-97 (2001).
Pubchem, CID-58901647, create date Aug. 19, 2012.
Qing, et al., "A Suzuki Coupling Approach to Trifluoromethyl Derivative of Targretin (LGD 1069).", Bioorganic & Medicinal Chemistry. 17(16), 2117-2120 (1997).
Rendi, et al., "The selective estrogen receptor modulator arzoxifene and the rexinoid LG100268 cooperate to promote transforming growth factor beta-dependent apoptosis in breast cancer", Cancer Res 64(10), 3566-3571 (2004).
Repa, et al., "Regulation of mouse sterol regulatory element-binding protein-1c gene (SREBP-1c) by oxysterol receptors, LXRalpha and LXRbeta", Genes Dev 14(22), 2819-2830 (2000).
Rigas, "Emerging role of rexinoids in non-small cell lung cancer: focus on bexarotene", Oncologist 10, 22-33 (2005).
Rizvi, et al., "A Phase I study of LGD1069 in adults with advanced cancer", Clin. Cancer Res. 5, 1658-1664 (1999).
Sacchetti, et al., "Nurr1 enhances transcription of the human dopaminetransporter gene through a novel mechanism", J. Neurochem. 76,1565-1572 (2001).
Safaryn, et al., "A convenient synthesis of (±) ascochlorin", Tetrahedron 42(10), 2635-2642 (1986).
Saijo, et al., "A Nurr1/CoREST pathway in microglia and astrocytes protects dopaminergicneurons from inflammation-induced death", Cell 137, 47-59 (2009).
Sakaki, et al., "Synthesis and Structure-activity Relationship of Nocel RXR antagonists: orally active antidiabetic and antiobesity agents.", Bioorg Med Chem Lett 17, 4804-4807 (2007).
Sakurada, et al., "Nurr1, an orphan nuclear receptor, is atranscriptional activator of endogenous tyrosine hydroxylase in neuralprogenitor cells derived from the adult brain", Development 126, 4017-4026 (1999).
Gorman, et al., "In vitro metabolic characterization, phenotyping, and kinetic studies of 9cUAB30, a retinoid X receptor-specific retinoid", Drug Metabolism & Disposition 35(7), 1157-1164 (2007).
Grenningloh, et al., "Cutting Edge: Inhibition of the Retinoid X Receptor (RXR) Blocks T Helper 2 Differentiation and Prevents Allergic Lung Inflammation", J. Immunol. 176, 5161-5166 (2006).
Grubbs, et al., "9cUAB30, an RXR specific retinoid, and/or tamoxifen in the prevention of methylnitrosourea-induced mammary cancers", Cancer Letters 201, 17-24 (2003).
Guibert, et al., "KRAS Mutations in Lung Adenocarcinoma: Molecular and Epidemiological Characteristics, Methods for Detection, and Therapeutic Strategy Perspectives", Curr Mol Med 15(5), 418-432 (2015).
Hansen, et al., "The low-toxicity 9-cis UAB30 novel retinoid down-regulates the DNA methyltransferases and has antitelomerase activity in human breast cancer cells", International Journal of Oncology 30(3), 641-650 (2007).
Heck, et al., "Modeling, Synthesis, and Biological Evaluation of Potential Retinoid X Receptor (RXR)-Selective Agonists: Analogues of 4-[1-(3,5,5,8,8-Pentamethyl-5,6,7,8-tetrahydro-2-naphthyl)ethynyl]benzoic Acid (Bexarotene) and 6-(Ethyl(5,5,8,8-tetrahydronaphthalen-2-y", J Med Chem 59(19), 8924-8940 (2016).
Heller, et al., "Synthetic retinoids in dermatology.", Canadian Medical Association Journal 132(10), 1129-1136 (1985).
Heo, et al., "Effect of bexarotene on differentiation of glioblastoma multiforme compared with ATRA", Clin Exp Metastasis 33(5), 417-429 (2016).
Hermanson, et al., "Nurr1 regulates dopamine synthesis and storage in MN9Ddopamine cells", Exp. Cell Res. 288, 324-334 (2003).
Hintermann, et al., "Identification of a series of highly potent activators of the Nurr1 signaling pathway", Bioorg. Med. Chem. Lett. 17,193-196 (2007).
Huang, et al., "Retinoid X receptor gamma signaling accelerates CNS remyelination", Nature Neuroscience 14, 45-53 (2011).
Huang, et al., "Studies on the structure-activity relationship of retinoids—Hansch analysis and 3DQSAR studies on specific ligands of retinoid X receptor", CAS Scifinder Abstract 33, 442-448 (1998).
Iriki, et al., "The cell-cell interaction between tumor-associated macrophages and small cell lung cancer cells is involved in tumor progression via STAT3 activation", Lung Cancer 106, 22-32 (2017).
Jackman, et al., "Impact of epidermal growth factor receptor and KRAS mutations on clinical outcomes in previously untreated non-small cell lung cancer patients: results of an online tumor registry of clinical trials", Clin Cancer Res 15(16), 5267-5273 (2009).
Jin, et al., "Reaction mechanism of synthesizing hydroxyterepthalic acid monoester with high selectivity and its application", Huagong Xuebao (Chinese Edition with English Abstract) 63(10), 3337-3344 (2012).
Jong, et al., "Conformational effects on retinoid recepetor selectivity. 1. Effect of 9-double bond geometry on retinoid X receptor activity.", J Med Chem 36, 2605-2613, (1993).
Jurutka, et al., "Modeling, synthesis, and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene) and (E)-3-(3-(1,2,3,4-tetrahydro-1,1,4,", Journal of Medicinal Chemistry 56, 8432-8454 (2013).
Kadkhodaei, et al., "Nurr1 is required formaintenance of maturing and adult midbrain dopamine neurons", J. Neurosci. 29, 15923-15932 (2009).
Kagechika, et al., "Retinobenzoic acids. 1. Structure-activity relationships of aromatic amides with retinoidal activity", J Med Chem 31, 2182-2192 (1988).
Kakuta, et al., "RXR Partial Agonist CBt-PMN Exerts Therapeutic Effects on Type 2 Diabetes without the Side Effects of RXR Full Agonists", ACS Medicinal Chemistry Letters 3, 427-432 (2012).

(56) References Cited

OTHER PUBLICATIONS

Kakuta, "Western-style Chinese (Kampo) medicine targeting retinoid X receptors (RXRs)", 248th ACS National Meeting, MEDI 102, San Francisco, CA. (Aug. 10-14, 2014).

Kamphorst, et al., "Proliferation of PD-1+ CD8 T cells in peripheral blood after PD-1-targeted therapy in lung cancer patients", Proc Natl Acad Sci USA 114(19), 4993-4998 (2017).

Kapetanovic, et al., "Murine Oncogenicity and Pharmacokinetics Studies of 9-cis-UAB30, an RXR Agonist, for Breast Cancer Chemoprevention", International Journal of Toxicology 29(2), 157-164 (2010).

Kawata, et al., "RXR partial agonist produced by side chain repositioning of alkoxy RXR full agonist retains antitype 2 diabetes activity without the adverse effects", J Med Chem 58(2), 912-926 (2015, epub 2014).

Keenan, et al., "Conformational Preferences in a Benzodiazepine Series of Potent Nonpeptide Fibrinogen Receptor Antagonists.", J Med Chem 42, 545-559, (1999).

Khuri, et al., "Multi-Institutional Phase I/II Trial of Oral Bexarotene in Combination With Cisplatin and Vinorelbine in Previously Untreated Patients With Advanced Non-Small-Cell Lung Cancer", Journal of Clinical Oncology 19, 2626-2637 (2001).

Kiick, et al. "Incorporation of azides into recombinant proteins for chemoselective modification by the Staudinger ligation", Proc. Natl. Acad. Sci. U.S.A. 99(1), 19-24 (2002).

Kishi, et al., "Significance of the progesterone receptor and epidermal growth factor receptor, but not the estrogen receptor, in chemically induced lung carcinogenesis in female A/J mice", Oncol Lett 8(6), 2379-2386 (2014).

Kobayashi, et al., "Positron emission tomography to elucidate pharmacokinetic differences of regioisomeric retinoid x receptor agonists", ACS Med Chem Lett 6(3), 334-338 (2015).

Koch, et al., "Identification of the First Retinoid X Receptor Homodimer Antagonist", J Med Chem 39(17), 3229-3234 (1996).

Koch, et al., "Synthesis of Retinoid X Receptor-Specific Ligands That Are Potent Inducers of Adipogenesis in 3T3-L1 Cells", Journal of Medicinal Chemistry 42, 742-750 (1999).

Kolesar, et al., "A pilot, first-in-human, pharmacokinetic study of 9cUAB30 in healthy volunteers", Cancer Prevention Research 3(12), 1565-1570 (2010).

Kowanetz, et al., "Granulocyte-colony stimulating factor promotes lung metastasis through mobilization of Ly6G +Ly6C+ granulocytes", Proc Natl Acad Sci USA 107(50), 21248-21255 (2010).

La Vista-Picard, et al., "The receptor-DNA complex determines the retinoid response: a mechanism for the diversification of the ligand signal.", Molecular and Cellular Biology 16(8), 4137-4146 (1996).

Lagu, et al., "RXR-LXR heterodimer modulators for the potential treatment of dyslipidemia", Bioorganic & Medicinal Chemistry Letters 17, 3497-3503 (2007).

Le, "Decreased NURR1 gene expressionin patients with Parkinson's disease", J. Neurol. Sci. 273, 29-33 (2008).

Le, "Mutations in NR4A2 associated withfamilial Parkinson disease", Nat. Genet. 33, 85-89 (2003).

Lehmann, et al., "Retinoids selective for retinoid X receptor pathways.", Science 258, 1944-1946 (1992).

Leid et al., "Multiplicity Generates Diversity in the Retinoic Acid Signaling Pathways", Trends Biochem. Sci. 17, 427-433 (1992).

Lerner, et al., "Bexarotene as add-on to antipsychotic treatment in schizophrenia patients: a pilot open-label trial.", Clinical Neuropharmacology 31(1), 25-33 (2008).

Lerner, et al., "The retinoid X receptor agonist bexarotene relieves positive symptoms of schizophrenia: a 6-week, randomized, double-blind, placebo-controlled multicenter trial", The Journal of Clinical Psychiatry 74(12), 1224-1232 (2013).

Li, et al., "Functional Evidence for Retinoid X Receptor (RXR) as a Nonsilent Partner in the Thyroid Hormone Receptor/RXR Heterodimer", Mol. Cell. Biol. 22, 5782-5792 (2002).

Liby, et al., "A new rexinoid, NRX194204, prevents carcinogenesis in both the lung and mammary gland", Clin Cancer Res 13(20), 6237-6243 (2007).

Liby, et al., "Rexinoids for prevention and treatment of cancer: opportunities and challenges", Curr Top Med Chem 17(6), 721-730 (2017, available online 2016).

Liby, et al., "Synthetic Triterpenoids Prolong Survival in a Transgenic Mouse Model of Pancreatic Cancer", Cancer Prevention Research 3(11), 1427-1434 (2010).

Liby, et al., "Triterpenoids and rexinoids as multifunctional agents for the prevention and treatment of cancer", Nat Rev Cancer 7(5), 357-369 (2007).

Liby, et al., "Triterpenoids CDDO-methyl ester or CDDO-ethyl amide and rexinoids LG100268 or NRX194204 for prevention and treatment of lung cancer in mice", Cancer Prev Res (Phila) 2(12), 1050-1058 (2009).

Lindeblad, et al., "Assessment of oral toxicity and safety of 9-cis-UAB30, a potential chemopreventive agent, in rat and dog studies", Drug and Chemical Toxicology 34(3), 300-310 (2011).

Lippert, et al., "Silicon Analogues of the RXR-Selective Retinoid Agonist SR11237 (BMS649): Chemistry and Biology", ChemMedChem 4, 1143-1152 (2009).

Sanders, et al., "A Phase 1 Clinical Study of the Retinoid X Receptor (RXR) Selective Agonist IRX4204 in Patients with Early Parkinson's Disease (PD) (P2.342)", http://n.neurology.org/content/86/16_Supplement/P2.342, First published Apr. 4, 2016.

Schimmel, et al., "4.5 kb of the rat tyrosine hydroxylase 5' flanking sequencedirects tissue specific expression during development and containsconsensus sites for multiple transcription factors", Mol. Brain Res. 74,1-14 (1999).

Schinelli, et al., "1-Methyl-4-phenyl-1,2,3,6-tetrahydropyridine metabolism and 1-methyl-4-phenylpyridinium uptake in dissociated cell cultures from the embryonic mesencephalon", J. Neurochem. 50(6), 1900-1907 (1988).

Sherman, et al., "Central hypothyroidism associated with retinoid X receptor-selective ligands", N. Engl. J. Med. 340(14), 1075-1079 (1999).

Shibakura, et al., "Anticoagulant Effects of Synthetic Retinoids Mediated via Different Receptors on Human Leukemia and Umbilical Vein Endothelial Cells.", Blood 90(4), 1545-1551 (1997).

Simone, "Oncology: Introduction, Cecil Textbook of Medicine", 20th Edition, vol. 1, 1004-1010 (1996).

Sleiman, et al., "Characterisation of a novel NR4A2 mutation in Parkinson's diseasebrain", Neurosci. Lett. 457, 75-79 (2009).

Sporn, "Retinoids and Cancer Prevention.", Cancer Journal for Clinicians 29(2), 120-125 (1979).

Svensson, et al., "Crystal structure of the heterodimeric complex of LXRa and RXRb ligand-binding domains in a fully agonistic conformation", EMBO J. 22(18), 4625-4633 (2003).

Takahasi, et al., "2,5-Diaryl-1,3,2-dioxaborinanes: A New Series of Liquid Crystals.", Bull Chem Soc 62(12), 3896-3901 (1989).

Takamatsu, et al., "The first potent subtype-selective retinoid X receptor (RXR) agonist possessing a 3-isopropoxy-4-isopropylphenylamino moiety, NEt-3IP (RXRalpha/beta-dual agonist)", ChemMedChem 3(5), 780-787 (2008).

Tan, et al., "Monitoring interactions between receptor tyrosine kinases and their downstream effector proteins in living cells using bioluminescence resonance energy transfer", Mol. Pharmacol. 72 (6), 1440-1446 (2007).

Tang, et al., "Myeloid-derived suppressor cell and macrophage exert distinct angiogenic and immunosuppressive effects in breast cancer", Oncotarget 8(33), 54173-54186 (2017).

Thacher, et al., "Receptor Specificity of Retinoid-Induced Epidermal Hyperplasia: Effect of RXR-Selective Agonists and Correlation with Topical Irritation", Journal Pharmacology and Experimental Therapeutics 282(2), 528-534 (1997).

Thalesnano Nanotechnology Inc., "H-Cube Continuous-flow hydrogenation reactor", www.thalesnano.com/h-cube, Published: Apr. 9, 2006, Retrieved: Dec. 29, 2014.

Thomas, "Retinoid Metabolism: a balancing act.", Nature Genetics 31, 7-8 (2002).

Thompson, et al., "Distinct retinoid X receptor activation function-2 residues mediate transactivation in homodimeric and vitamin D receptor heterodimeric contexts", J. Mol. Endocrinol. 27(2), 211-227 (2001).

(56) References Cited

OTHER PUBLICATIONS

Traynelis, et al., "Ylide Methylation of Aromatic Nitro Compounds.", J Org Chem 31, 243-247 (1964).
Uray, et al., "Retinoids and rexinoids in cancer prevention: from laboratory to clinic", Semin Oncol 43(1), 49-64 (2016, epub 2015).
Vahlquist, "What are Natural Retinoids.", Dermatology 199(Suppl 1), 3-11 (1999).
Vuligonda, et al., "Enantioselective Synthesis of Potent Retinoid X Receptor Ligands: Differential Biological Activities of Individual Antipodes", J. Med. Chem. 44, 2298-2303 (2001).
Wagner, et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene).", J Med Chem 52(19), 5950-5966 (2009).
Wallen-Mackenzie, et al., "Nurr1-RXR heterodimers mediate RXR ligand-induced signaling in neuronal cells", Genes & Development 17, 3036-3047 (2003).
Wang, et al., "IL-6 Mediates Macrophage Infiltration after Irradiation via Up-regulation of CCL2/CCL5 in Non-small Cell Lung Cancer", Radiat Res 187(1), 50-59 (2017).
Wang, et al., "Structure and function ofNurr1 identifies a class of ligand-independent nuclear receptors", Nature 423, 555-560 (2003).
Wang, et al., "Up regulation of IL-6 is involved in di (2-ethylhexyl) phthalate (DEHP) induced migration and invasion of non small cell lung cancer (NSCLC) cells", Biomed Pharmacother 89, 1037-1044 (2017).
White, et al., "Identification of the retinoic acid-inducible all-trans-retinoic acid 4-hydroxylase.", Journal of Biological Chemistry 271, 29922-29927 (1996).
Whitworth, et al., "The impact of novel retinoids in combination with platinum chemotherapy on ovarian cancer stem cells", Gynecologic Oncology 125, 226-230 (2012).
Winum, et al., "Synthesis of New Targretin® Analogues that Induce Apoptosis in Leukemia HL-60 Cells.", Bioorg Med Chem Lett 12, 3529-3532 (2002).
Wojcik, et al., "IL-6 and VEGF in small cell lung cancer patients", Anticancer Res 30(5), 1773-1778 (2010).
Wu, et al., "An intermittent approach for cancer chemoprevention", Nat Rev Cancer 11(12), 879-885 (2011).
Wu, et al., "The retinoid X receptor-selective retinoid, LGD1069, prevents the development of estrogen receptor-negative mammary tumors in transgenic mice", Cancer Res 62(22), 6376-6380 (2002).
Yamauchi, et al., "Inhibition of RXR and PPARgamma ameliorate diet-induced obesity and type 2 diabetes", J. Clin. Invest. 108, 1001-1013 (2001).
Yen, et al., "A selective retinoid X receptor agonist bexarotene (Targretin) prevents and overcomes acquired paclitaxel (Taxol) resistance in human non-small cell lung cancer", Clinical Cancer Research 10(24), 8656-8664 (2004).
Yen, et al., "A Selective Retinoid X Receptor Agonist Bexarotene (Targretin) Prevents and Overcomes Acquired Paclitaxel (Taxol) Resistance in Human Non-Small Cell Lung Cancer.", British Journal of Cancer 94, 654-660 (2006).
Yen, et al., "Synergistic effect of a retinoid X receptor-selective ligand bexarotene (LGD1069, Targretin) and paclitaxel (Taxol) in mammary carcinoma", Breast Cancer Res. Treat. 88, 141-148 (2004).
Yeo, et al., "Chemopreventive effect of phosphodieasterase-4 inhibition in benzo(a)pyrene-induced murine lung cancer model", Exp Lung Res 40(10), 500-506 (2014).
You, et al., "Activation of the Ki-ras protooncogene in spontaneously occurring and chemically induced lung tumors of the strain A mouse", Proc Natl Acad Sci USA 86(9), 3070-3074 (1989).
Zaynagetdinov, et al., "A critical role for macrophages in promotion of urethane-induced lung carcinogenesis", J Immunol 187(11), 5703-5711 (2011).
Zetterstrom, et al., "Dopamine neuronagenesis in Nurr1-deficient mice", Science 276, 248-250 (1997).
Zhang, et al., "Aerosolized bexarotene inhibits lung tumorigenesis without increasing plasma triglyceride and cholesterol levels in mice", Cancer Prev Res (Phila) 4(2), 270-276 (2011, epub 2010).
Zhang, et al., "Induction of Apoptosis by Bexarotene in Cutaneous T-Cell Lymphoma Cells.", Clin Cancer Res 8, 1234-1240 (2002).
Zhang, et al., "Syntheses of isotopically labeled 4-[1-(3,5,5,8,8-pentamethyl-5,6,7,8-tetrahydro-2-naphthyl)ethenyl] benzoic acid (LGD1069), a potent retinoid x receptor-selective ligand", Journal of Labelled Compounds and Radiopharmaceuticals 36(7), 701-712 (1995).
Zimmermann, et al., "A yeast strain for simultaneous detection of mitotic crossing over, mitotic gene conversion, and reverse mutation", Mutat. Res. 28, 381-388, (1975).
Zimmermann, "Procedures used in the induction of mitotic recombination and mutation in the yeast Saccharomyeces cerevisiae", Mutat. Res. 31, 71-86 (1975).
Adams, et al., "Discovery of GSK1070916, a Potent and Selective Inhibitor of Aurora B/C Kinase", J. Med. Chem. 53, 3973-4001 (2010).
Altucci, et al., "RAR and RXR modulation in cancer and metabolic disease.", Nature Rev Drug Discovery 6, 793-810 (2007).
Amoutzias, "A protein interaction atlas for thenuclear receptors: properties and quality of a hub-based dimerisationnetwork", BMC Syst. Biol. 1, 34, 12 pages (2007).
Assaf, "Minimizing adverse side-effects of oral bexarotene in cutaneous T-cell lymphoma: an expert opinion.", Br. J. Dermatol. 155, 261-266 (2006).
Atigadda, et al., "Conformationally Defined Retinoic Acid Analogues. 5. Large-Scale Synthesis and Mammary Cancer Chemopreventive Activity for (2E,4E,6Z,8E)-8-(3',4'-Dihydro-1'(2'H)-naphthalen-1'-ylidene)-3,7-dimethyl-2,4,6-octatrienoic Acid (9cUAB30)", Journal of Medicinal Chemistry 46(17), 3766-3769 (2003).
Atigadda, et al., "Methyl substitution of a rexinoid agonist improves potency and reveals site of lipid toxicity", Journal of Medicinal Chemistry 57(12), 5370-5380 (2014).
Batie, et al., "Synthesis and biological evaluation of halogenated curcumin analogs as potential nuclear receptor selective agonists", Bioorganic Med Chem 21(3), 693-702 (2013, epub 2012).
Blumenschein, et al., "Phase III trial comparing carboplatin, paclitaxel, and bexarotene with carboplatin and baclitaxel in chemotherapy-naive patients with advanced or metastatic non-small-cell lung cancer: SPIRIT II", J Clin Oncol 26(11), 1879-1885 (2008).
Boehm, et al., "Synthesis and Structure-Activity Relationships of Novel Retinoid X Receptor-Selective Retinoids.", Journal of Medicinal Chemistry 37, 2930-2941 (1994).
Brown, et al., "Combination Chemoprevention of HER2/neu-Induced Breast Cancer Using a Cyclooxygenase-2 Inhibitor and a Retinoid X Receptor—Selective Retinoid", Cancer Prev Res (Phila) 1(3), 208-214 (2008).
Bruson, et al., "Cycli-Alkylation of Aromatic Compounds by the Friedel and Crafts Reaction", J Am Chem Soc 62(1), 36-44 (1940).
Caetano, et al., "L6 Blockade Reprograms the Lung Tumor Microenvironment to Limit the Development and Progression of K-ras-Mutant Lung Cancer", Cancer Res 76(11), 3189-3199 (2016).
Cao, et al "The Rexinoids LG100268 and LG101506 Inhibit Inflammation and Suppress Lung Carcinogenesis in A/J Mice", Cancer Prev Res (Phila) 9(1), 105-114 (2016, epub 2015).
Carpentier, "The glucocorticoid receptor is a co-regulator of the orphan nuclear receptor Nurr1", J. Neurochem. 104, 777-789 (2008).
Cesario, et al., "Differentiation and growth inhibition mediated via the RXR:PPARgamma heterodimer in colon cancer", Cancer Letters 240(2), 225-233 (2006).
Chemical Abstract, STN Registry Database, RN 1207107-44-5, 1 page, entered into database Feb. 22, 2010.
Chu, "Nurr1 in Parkinson's disease and relateddisorders", J. Comp. Neurol. 494, 495-514 (2006).
Claudel, et al., "Reduction of atherosclerosis in apolipoprotein E knowout mice by activation of the retinoid X receptor", PNAS 98 (5), 2610-2615 (2001).
Cramer, et al., "ApoEdirected therapeutics rapidly clear β-amyloid and reverse deficits in AD mouse models", Science 335, 1503-1506 (2012).

(56) References Cited

OTHER PUBLICATIONS

Crunkhorn, "RXR agonist reverses Alzheimer's disease", Nature Reviews Drug Discovery 11, 271 (2012).
Dai, et al., "Liver X receptor β protects dopaminergic neurons in a mouse model of Parkinson disease", Proc. Natl. Acad. Sci. U.S.A. 109, 13112-13117 (2012).
Daiss, et al., "Synthesis, Crystal Structure Analysis, and Pharmacological Characterization of Disila-bexarotene, a Disila-Analogue of the RXR-Selective Retinoid Agonist Bexarotene.", Organometallics 24, 3192-3199 (2005).
Danziger, "Automated Site-Directed Drug Design: A General Algorithm for Knowledge Acquisition about Hydrogen-Bonding Regions at Protein Surfaces", Proceedings of the Royal Society of London, Series B, Biological Sciences, 236(1283), 101-113 (1989).
Dawson, et al., "Conformational effects on retinoid receptor selectivity. 2. Effects of retinoid bridging group on retinoid X receptor activity and selectivity.", J Med Chem 38, 3368-3383 (1995).
Dawson, et al., "sp2-Bridged Diaryl Retinoids: Effects of Bridge-Region Substitution on Retinoid X Receptor (RXR) Selectivity", Bioorganic & Medicinal Chemistry Letters 10, 1307-1310 (2000).
Dawson, et al., "The Receptor-DNA Determines the Retinoid Response: a Mechanism for the Diversification of the Ligand Signal.", Molecular and Cellular Biology 16(8), 4137-4146 (1996).
Dimick, et al., "On the Meaning of Affinity: Cluster Glycoside Effects and Concanavalin A.", J Am Chem Soc 121, 10286-10296 (1999).
Dragnev, et al., "A Proof-of-Principle Clinical Trial of Bexarotene in Patients with Non-Small Cell Lung Cancer", Clin. Cancer Res. 13, 1794-1800 (2007).
Dragnev et al., "Bexarotene plus erlotinib suppress lung carcinogenesis independent of KRAS mutations in two clinical trials and transgenic models", Cancer Prev Res (Phila) 4(6), 818-828 (2011).
Dubois, et al., "Identification of a potent agonist of the orphan nuclear receptor Nurr1", ChemMedChem 1, 955-958 (2006).
Duvic, et al., "BexaroteneWorldwide Study Group. Bexarotene is effective and safe for treatmentof refractory advanced-stage cutaneous T-cell lymphoma: multinationalphase II-III trial results", J. Clin. Oncol. 19, 2456-24571 (2001).
Edelman, et al., "Phase II trial of the novel retinoid, bexarotene, and gemcitabine plus carboplatin in advanced non-small-cell lung cancer", J Clin Oncol 23(24), 5774-5778 (2005).
Egea, et al., "Molecular recognition of agonist ligands by RXRs", Mol. Endocrinol. 16, 987-997 (2002).
Esteva et al., "Multicenter Phase II Study of Oral Bexarotene for Patients With Metastatic Breast Cancer", Journal of Clinical Oncology 21(6), 999-1006 (2003).
Evans, et al., "Nuclear Receptors, RXR, and the Big Bang", Cell 157(1), 255-266 (2014).
Fantini, et al., "Bexarotene Blocks Calcium-Permeable Ion Channels Formed by Neurotoxic Alzheimer's beta-Amyloid Peptides", ACS Chemical Neuroscience 5(3), 216-224 (2014).
Farmer, et al., "Aza-retinoids as novel retinoid X receptor-specific agonists", Bioorg. Med. Chem. Lett. 16, 2352-2356 (2006).
Faul, et al., "Synthesis of Novel Retinoid X Receptor-Selective Retinoids.", J Org Chem 66, 5772-5782 (2001).
Feng-Ling, et al., "A Suzuki Coupling Approach to Trifluoromethyl Derivative of Targretin (LGD 1069)", Bioorganic and Medicinal Chemistry Letters, 7 (16), 2117-2120 (1997).
Field, et al., "LXR/RXR ligand activation enhances basolateral efflux of beta-sitosterol in CaCo-2 cells", J. Lipid Res. 45, 905-913 (2004).
Forman, et al., "Unique response pathways are established by allosteric interactions among nuclear hormone receptors", Cell 81, 541-550 (1995).
Friling, et al., "Activation of Retinoid X Receptor increases dopamine cell survival in models for Parkinson's disease", BMC Neurosci. 10, 146-153 (2009).
Fujii, et al., "Effect of a retinoid X receptor partial agonist on airway inflammation and hyperresponsiveness in a murine model of asthma", Respir Res 18(23), 10 pages (2017).
Fujii, et al., "Metabolic inactivation of retinoic acid by a novel P450 differentially expressed in developing mouse embryos.", The EMBO Journal 16(14), 4163-4173 (1997).
Furmick, et al., "Modeling, synthesis and biological evaluation of potential retinoid X receptor-selective agonists: novel halogenated analogues of 4-[1-(3,5,5,8,8-pentamethyl-5,6,7,8-tetrahydro-2-naphthyl)ethynyl]benzoic acid (bexarotene)", ChemMedChem 7(9), 1551-1566 (2012).
Galleguillos, "Nurr1 regulates RET expression in dopamine neurons of adult ratmidbrain", J. Neurochem. 114, 1158-1167 (2010).
Gandi, "Reactions of Some Aromatic Nitro Compounds with Alkali Metal Amides.", J Org Chem 44(25), 4705-4707 (1979).
Garcia, et al., "Pyrazine arotinoids with inverse agonist activities on the retinoid and rexinoid receptors", Chembiochem 10, 1252-1259 (2009).
Gernert, et al., "Design and Synthesis of Fluorinated RXR Modulators.", Bioorg Med Chem Lett 13, 3191-3195 (2003).
Gorelik, et al., "Susceptibility of Various Strains of Mice to Urethan-Induced Lung Tumors and Depressed Natural Killer Cell Activity", J Natl Cancer Inst 67(6), 1317-1322 (1981).

* cited by examiner

ISOCHROMAN COMPOUNDS AND METHODS OF USE THEREOF

PRIORITY OF INVENTION

This application claims priority to U.S. Provisional Application No. 62/449,495, filed 23 Jan. 2017. The entire content of this provisional application is hereby incorporated herein by reference.

BACKGROUND OF THE INVENTION

The human retinoid X receptors (hRXRs) consist of three identified isoforms (α, β, γ) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Six rexinoids described in the literature include Bexarotene (60), CD3254 (61), LGD100268 (62), a pyridyl-bexarotene analog (1), an unsaturated bexarotene analog (2), and the mono-fluorinated bexarotene analog (3).

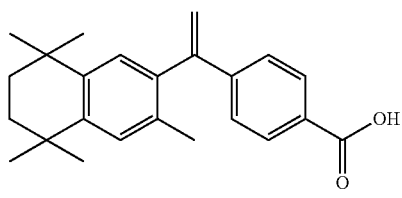

Bexarotene

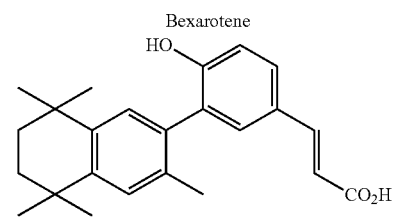

CD 3254

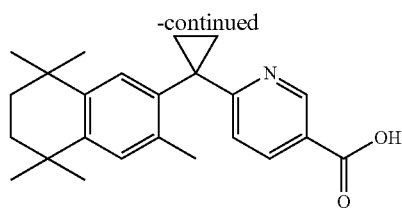

LGD100268

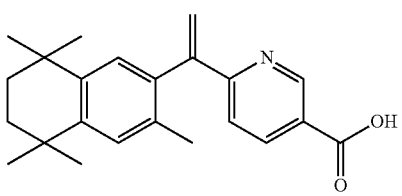

1

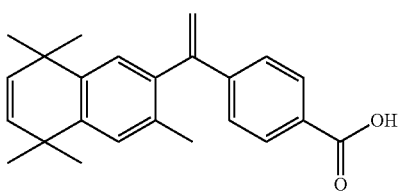

2

3

Bexarotene has been documented to have an $EC_{50}$ of 33, 24 and 25 nm for the RXR α,β,γ subtypes, respectively, and a $K_d$ of 14, 21, and 29 nm for the RXR α,β,γ subtypes, respectively, in a CV-1 cell line (Boehm, M. F., et al., "Synthesis and Structure-Activity Relationships of Novel Retinoid X Receptor-Selective Retinoids" *J. Med. Chem.* 1994, 37, 2930-2941). CD3254 appears to have an $EC_{50}$ on the order of 10 nm for the hRXRβ isoform (Santin, E. P., et al., "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers" *J. Med. Chem.* 2009, 52, 3150-3158). LGD100268 and 1 have been documented to have $EC_{50}$s of 4, 3, and 4 nm and 6, 9, and 5 nm for the RXR α,β,γ subtypes, respectively, and $K_d$s of 3, 3, and 3 nm and 22, 61, and 39 nm for the RXR α,β,γ subtypes, respectively, in a CV-1 cell line (Boehm, M. F., et al., "Design and Synthesis of Potent Retinoid X Receptor Selective Ligands That Induce Apoptosis in Leukemia Cells" *J. Med. Chem.* 1995, 38, 3146-3155). While the unsaturated-bexarotene analog (2) has been reported, its ability to serve as an RXR agonist has not been published. Finally, the mono-fluorinated bexarotene analog (3) has an $EC_{50}$ of 43 nm and a $K_d$ of 12 nm in hRXR in Caco-2 cells (Wagner, C. E., et al., "Modeling, Synthesis and Biological Evaluation of Potential Retinoid X Receptor (RXR) Selective Agonists: Novel Analogues of 4-[1-(3,5,5,8,8-Pentamethyl-5,6,7,8-tetrahydro-2-naphthyl) ethynyl]benzoic Acid (Bexarotene)" *J. Med. Chem.* 2009, 52, 5950-5966).

Currently there is a need for additional chemical agents that are useful for treating or preventing cancer or treating or preventing Alzheimer's disease. There is also a need for anti-cancer or anti-Alzheimer's agents that have enhanced activity or that have improved pharmacologic properties such as increased solubility or better bioavailability.

Additionally, studies suggest that the retinoid X receptor pathway is associated with CNS remyelination processes (see M. Natrajan, et al., *Brain*, 2015, 1-17; and J. K. Huang et al., Nature Neuroscience, 2010, 1) Currently there is a need for additional chemical agents that are useful for treating conditions associated with demyelination, such as, for example, multiple sclerosis.

SUMMARY OF THE INVENTION

This invention provides compounds for treating cancers, Alzheimer's disease, or conditions associated with demyelination.

Accordingly the invention provides a compound of invention which is a compound of formula I:

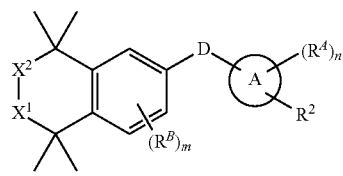

wherein:
$X^1$ is —O— and $X^2$ is —$CH_2$—;
or $X^1$ is —$CH_2$— and $X^2$ is —O—;
$R^2$ is —COOH, —B(OH)$_2$, or —$SO_3H$;
D is

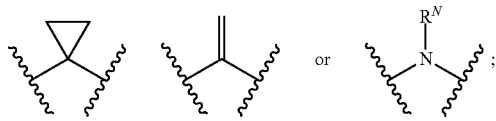

$R^N$ is ($C_1$-$C_6$)alkyl, ($C_3$-$C_6$)cycloalkyl, ($C_2$-$C_6$)alkenyl, or ($C_2$-$C_6$)alkynyl, wherein the ($C_1$-$C_6$)alkyl, ($C_3$-$C_6$)cycloalkyl, ($C_2$-$C_6$)alkenyl, and ($C_2$-$C_6$)alkynyl are optionally substituted with one or more groups independently selected from halo, hydroxy, nitro, cyano, and oxo (=O);
ring A is phenyl or 6-membered heteroaryl;
each $R^A$ is independently selected from the group consisting of halo, hydroxy, cyano, nitro, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)alkoxycarbonyl, and ($C_1$-$C_6$)alkanoyloxy, wherein the ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)alkoxycarbonyl, and ($C_1$-$C_6$)alkanoyloxy are optionally substituted with one or more groups independently selected from halo, hydroxy, nitro, cyano, ($C_1$-$C_6$)alkoxy, and oxo (=O);
each $R^B$ is independently selected from the group consisting of halo, hydroxy, cyano, nitro, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)alkoxycarbonyl, and ($C_1$-$C_6$)alkanoyloxy, wherein the ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)alkoxycarbonyl, and ($C_1$-$C_6$)alkanoyloxy are optionally substituted with one or more groups independently selected from halo, hydroxy, nitro, cyano, ($C_1$-$C_6$)alkoxy, and oxo (=O);
n is 0, 1, 2, 3, or 4; and
m is 0, 1, 2, 3, or 4;
or a salt thereof.

The invention also provides a pharmaceutical composition comprising a compound of the invention, or a pharmaceutically acceptable salt thereof, in combination with a pharmaceutically acceptable diluent or carrier.

The invention also provides a method for inhibiting cancer cell (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma), growth comprising contacting the cell in vitro or in vivo with an effective amount of a compound of the invention, or a salt thereof. The off-label use of bexarotene, a known RXR agonist, and retinoids in other cancers is currently being researched.

The invention also provides a method for treating cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) comprising administering to the mammal an effective amount of a compound of the invention, or a pharmaceutically acceptable salt thereof.

The invention also provides a method for treating cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) in need of such treatment comprising administering to the mammal an effective amount of a compound of the invention, or a pharmaceutically acceptable salt thereof.

The invention also provides a method for treating cancer (e.g., glioblastoma multiforme, breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) diagnosed with cancer comprising administering to the mammal an effective amount of a compound of the invention, or a pharmaceutically acceptable salt thereof.

The invention also provides a method for activating RXR in a cell comprising contacting the cell in vitro or in vivo with an effective amount of a compound of the invention, or a salt thereof.

The invention also provides a method for treating a condition associated with activating RXR in a cell comprising contacting the cell in vitro or in vivo with an effective amount of a compound of the invention, or a salt thereof.

The invention also provides a method for treating Alzheimer's disease in a human comprising administering to the human an effective amount of compound of the invention, or a pharmaceutically acceptable salt thereof.

The invention also provides a method for treating Alzheimer's disease in a human in need of such treatment comprising administering to the human an effective amount of compound of the invention, or a pharmaceutically acceptable salt thereof.

The invention also provides a method for treating Alzheimer's disease in a human diagnosed with Alzheimer's disease comprising administering to the human an effective amount of compound of the invention, or a pharmaceutically acceptable salt thereof.

The invention also provides a method for treating a disease associated with demyelination in a mammal (e.g. multiple sclerosis) comprising administering to the mammal an effective amount of compound of the invention, or a pharmaceutically acceptable salt thereof.

The invention also provides a method for treating a disease associated with demyelination (e.g. multiple sclerosis) in a mammal (e.g. a human) in need of such treatment comprising administering to the mammal an effective amount of compound of the invention, or a pharmaceutically acceptable salt thereof.

The invention also provides processes and novel intermediates that are useful for preparing the compounds of the invention.

DETAILED DESCRIPTION

The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "alkyl", by itself or as part of another substituent, means, unless otherwise stated, a straight or branched chain hydrocarbon radical, having the number of carbon atoms designated.

The term "alkenyl" refers to an unsaturated alkyl radical having one or more double bonds. Similarly, the term "alkynyl" refers to an unsaturated alkyl radical having one or more triple bonds.

The term "alkoxy" refers to an alkyl groups attached to the remainder of the molecule via an oxygen atom ("oxy").

The term "cycloalkyl" refers to a saturated all carbon ring having 3 to 6 carbon atoms (i.e., $(C_3-C_6)$carbocycle).

The term "6-membered heteroaryl ring" includes single aromatic rings with at least two carbon atoms and 1, 2, 3, or 4 heteroatoms selected from N, O or S.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; and heteroaryl can be pyrazinyl, pyridazine, triazine, pyridyl, or pyrimidinyl, or an N-oxide thereof.

In one embodiment, the invention provides a compound of formula I which is a compound of formula Ia:

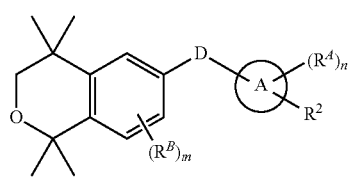

or a salt thereof.

In one embodiment, the invention provides a compound of formula I which is a compound of formula Ib:

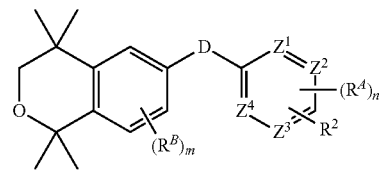

wherein $Z^1$ is N or CH;
$Z^2$ is N or CH;
$Z^3$ is N or CH; and
$Z^4$ is N or CH;
or a salt thereof.

In one embodiment, the invention provides a compound of formula I which is a compound of formula Ic

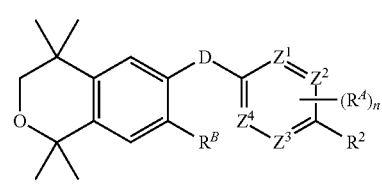

or a salt thereof.

In one embodiment, $R^2$ is —COOH.

In one embodiment, D is

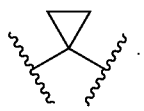 [SMILES: *C1(*)CC1]

In one embodiment, D is

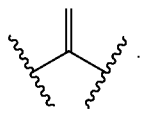

In one embodiment, D is

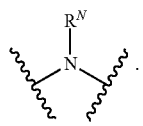

In one embodiment, $R^N$ is $(C_1-C_6)$alkyl that is optionally substituted with one or more groups independently selected from halo, hydroxy, nitro, cyano, and oxo (=O).

In one embodiment, $R^N$ is ethyl.

In one embodiment, ring A is 6-membered heteroaryl comprising 1 to 3 nitrogen atoms.

In one embodiment, ring A is

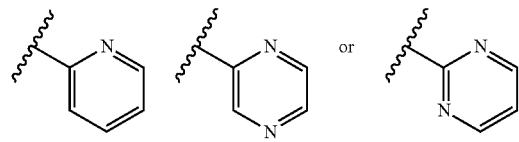

In one embodiment, A is phenyl.

In one embodiment, each $R^A$ is independently halo or hydroxyl.

In one embodiment, $R^A$ is —F.

In one embodiment, $R^B$ is $(C_1-C_6)$alkyl that is optionally substituted with one or more groups independently selected from halo, hydroxy, nitro, cyano, and oxo (=O).

In one embodiment, wherein $R^B$ is methyl.

In one embodiment, n is 0, 1, or 2.

In one embodiment, the compound of invention is selected from the group consisting of:

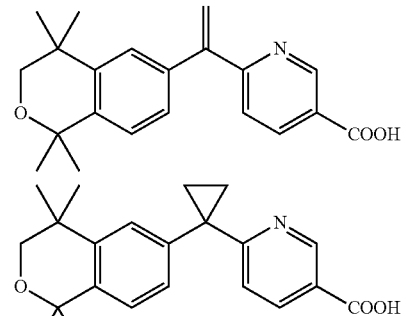

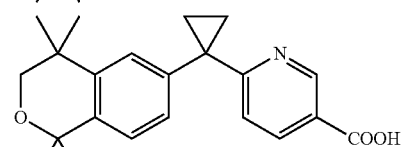

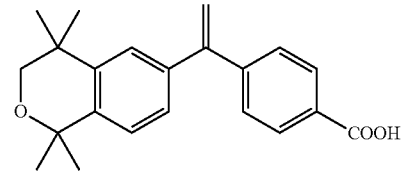

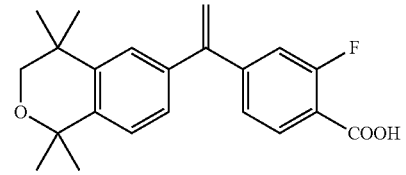

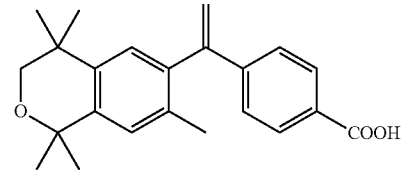

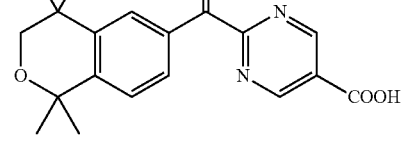

-continued

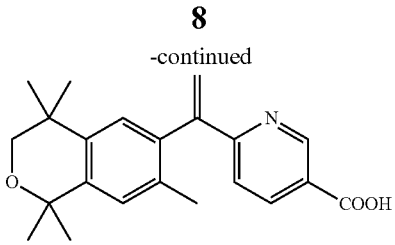

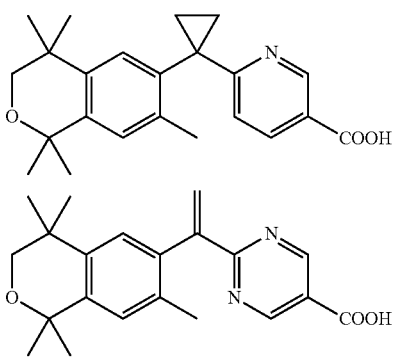

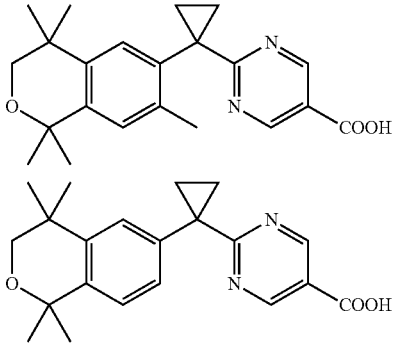

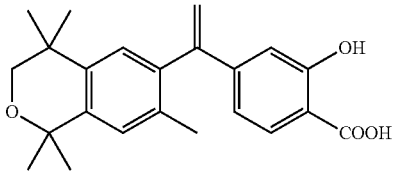

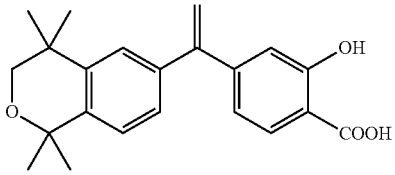

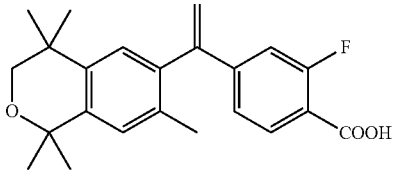

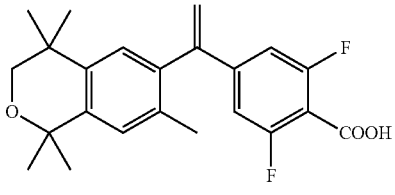

-continued

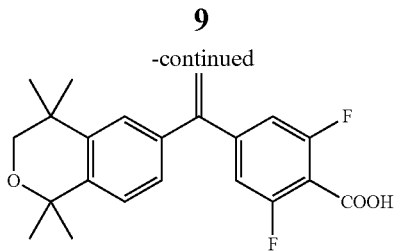
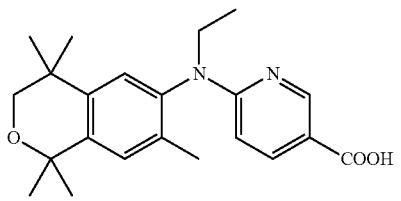
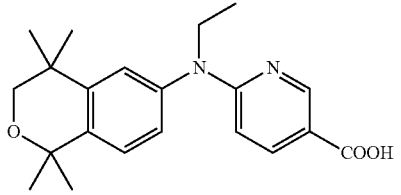
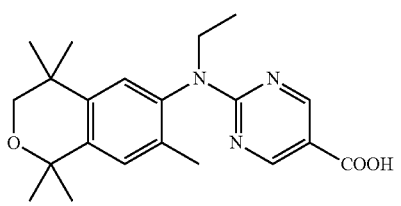
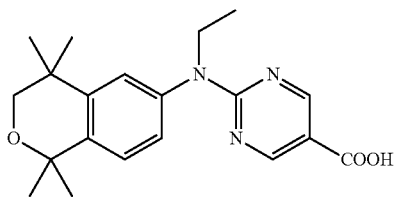
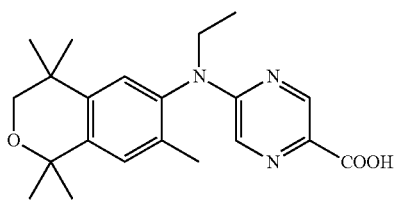
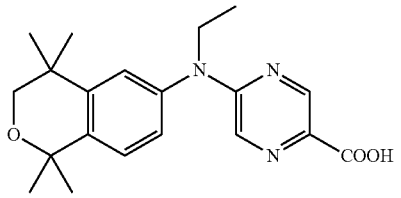
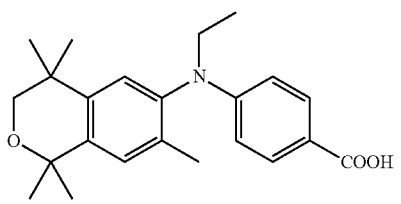

-continued

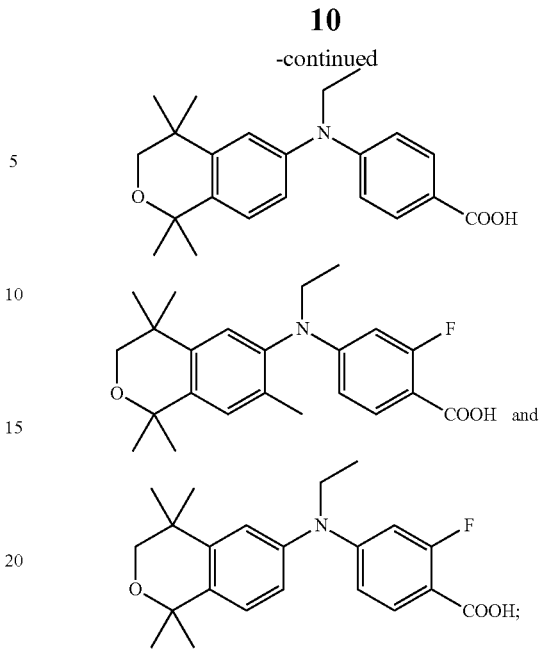

and salts thereof.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames *Salmonella*/microsome mutagenicity assay." Mutat. Res. 2000, 455, 29-60.)

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. In certain embodiments, compounds of the invention can be administered in combination with agents that are useful for the treatment of breast cancer. (Yen, W. et al. "Synergistic effect of a retinoid X receptor-selective ligand bexarotene (LGD1069, Targretin) and paclitaxel (Taxol) in mammary carcinoma" Breast Cancer Research and Treatment, 2004, 88, 141-148.) In certain embodiments, compounds of the invention can be administered in combination with agents that are useful for the treatment of lung cancer. (Yen, W.-C.; Corpuz, M. R.; Prudente, R. Y.; Cooke, T. A.; Bissonnette, R. P.; Negro-Vilar, A.; Lamph, W. W. "A Selective Retinoid X Receptor Agonist Bexarotene (Targretin) Prevents and Overcomes Acquired Paclitaxel (Taxol) Resistance in Human Non-Small Cell Lung Cancer." Clin. Cancer Res. 2004, 10, 8656-8664.). In certain embodiments, compounds of the invention can be administered in combination with agents that are useful for the treatment of glioblastoma multiforme. (*Clin Exp Metastasis,* 2016, 33, 417-429). In certain embodiments, compounds of the invention can be administered in combination with agents that are useful for the treatment of diabetes. (Mukherjee, R.; Davies, P. J. A.; Crombie, D. L.; Bischoff, E. D.; Cesario, R. M.; Jow, L.; Hamanns, L. G.; Boehm, M. F.; Mondon, C. E.; Nadzan, A. M.; Paterniti, J. R.; Heyman, R. A. "Sensitization of diabetic and obese mice to insulin by retinoid X receptor agonists." Nature 1997, 386, 407-410.) Accordingly, in one embodiment the invention also provides a composition comprising a compound of the invention, or a pharmaceutically acceptable salt thereof, at least one other therapeutic agent, and a pharmaceutically acceptable diluent or carrier. The invention also provides a kit comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to an animal to treat cancer or diabetes.

The ability of a compound of the invention to act as an RXR agonist (e.g. to promote or activate RXR, i.e., promote or activate RXR regulated gene expression) may be determined using pharmacological models which are well known to the art, or using Test A or Test B described below.

Test A. RXR Selective Agonist Assay (Mammalian Two-Hybrid Assay).

Compounds will be tested for RXR selective agonist activity via a mammalian two-hybrid assay in human colon cancer cells, HCT-116. The cell line is transfected with pCMVhRXR binding domain vector (BD), hRXR activation domain (AD), pFR-Luc reporter gene containing BD-binding sites, and a *renilla* control plasmid. Cells are transfected for 7 hours utilizing a liposome-mediated transfection protocol then exposed to either the ethanol vehicle or $10^{-7}$ M Bexarotene or the indicted analog. After 24 hours the cells are lysed and a luciferase assay is completed. Analog dependent RXR binding and homodimerization, as measured by luciferase output, is compared to the parent compound Bexarotene.

Test B. RXR Agonist Assay (RXRE-Luciferase Based Assay).

Compounds will be tested for RXR agonist activity via an RXRE-luciferase based system utilizing human colon cancer cells HCT-116. The cell line is transfected with hRXRα, an RXRE luciferase reporter gene, *renilla* control plasmid, and carrier DNA (pTZ18U). Cells are transfected for 7 hours utilizing a liposome-mediated transfection protocol then exposed to either the ethanol vehicle or $10^{-7}$M Bexarotene or the indicted analog. After 24 hours the cells are lysed and a luciferase assay is completed. Analog dependent, RXR-mediated transcription, as measured by luciferase output, is compared to the parent compound Bexarotene.

Compounds of invention can be prepared using known methods or using procedures analogous to those described herein. For example, compounds of invention can be prepared as illustrated in the following scheme.

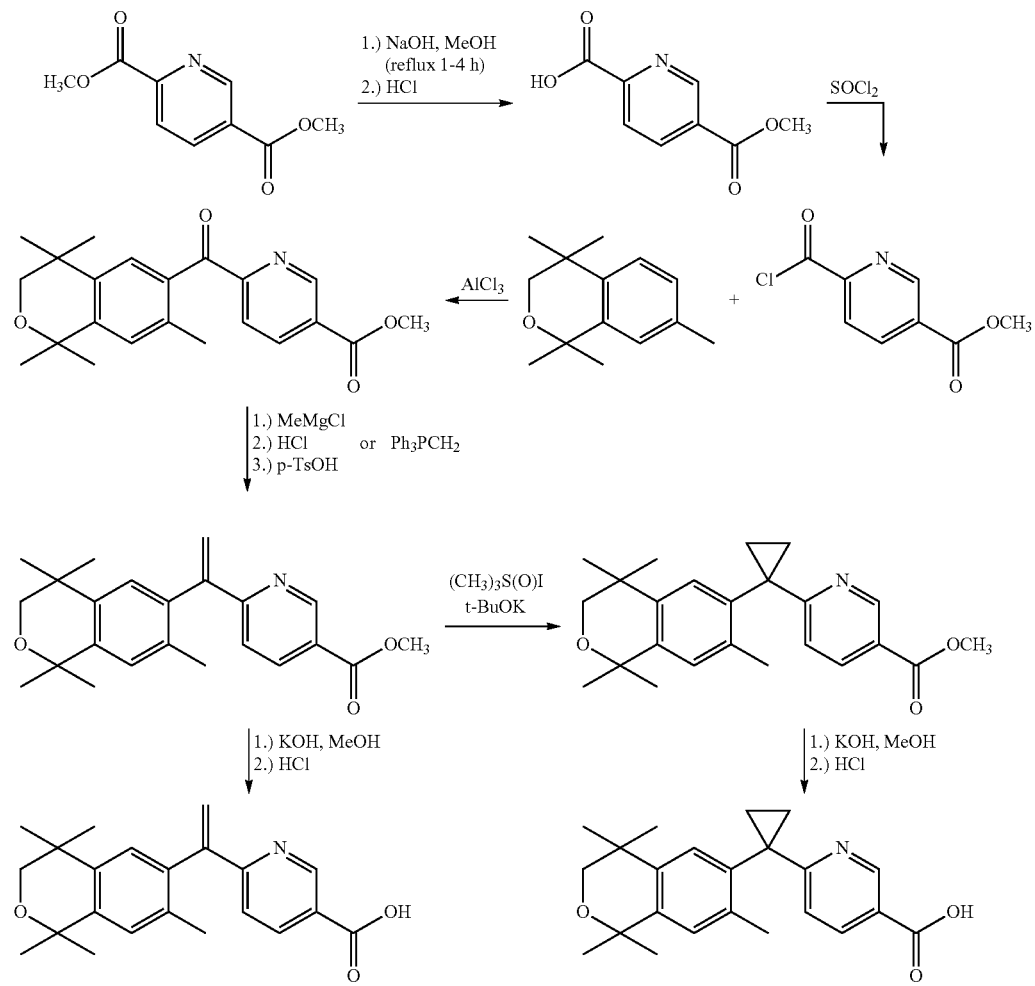

Compounds of the invention can also be prepared using techniques and intermediates similar to those described in International Patent Application Publication Numbers WO2004/093809, WO2011/103321, and WO2013/040227.

The invention will now be illustrated by the following non-limiting Examples.

EXAMPLES

Example 1. Preparation of Intermediate Compound 6-bromo-1,1,4,4,7-pentamethyl-isochroman (10)

An intermediate compound 6-bromo-1,1,4,4,7-pentamethyl-isochroman (10) can be used to prepared compounds of the invention. Compound 10 can be prepared as illustrated in the following scheme. Starting compound 9 1,1,4,4,7-pentamethyl-isochroman (97%) is commercially available (e.g. from Ark Pharm, Inc. (cat. No. AK461839)).

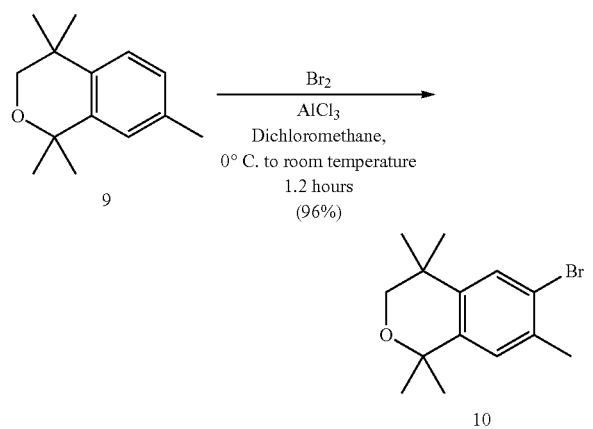

A modification of the procedure described by Pfhal and co-workers (International Patent Application Publication Numbers WO2004/093809) was used to prepare compound (10). To a 100 mL round bottom flask with a stir-bar and 1,1,4,4,7-pentamethyl-isochroman (9) (1.8253 g, 8.934 mmols) dissolved in dichloromethane (6.0 mL) and cooled to 0° C. in an ice-bath was added aluminum trichloride (0.258 g, 1.93 mmols) followed by the dropwise addition of bromine (0.5 mL, 9.7 mmols). The reaction mixture was allowed to warm to room temperature and was stirred for 1.2 hours after which time it was poured into 20 mL of a 40% ethyl acetate/hexanes solution. This solution was washed with saturated sodium sulfite (50 mL), the layers were separated, and the aqueous layer was extracted with ethyl acetate. The combined organic layers were washed with brine, dried over sodium sulfate, filtered and concentrated to give a crude product that was purified by column chromatography (150 mL SiO$_2$, hexanes:ethyl acetate 98:2) to give compound 10 (2.4289 g, 96%) as a white crystalline solid: $^1$H NMR (400 MHz, CDCl$_3$) δ 7.43 (s, 1H), 6.91 (s, 1H), 3.55 (s, 2H), 2.35 (s, 3H), 1.50 (s, 6H), 1.24 (s, 6H); $^{13}$C NMR (100.6 MHz, CDCl$_3$) δ 142.2, 140.8, 135.0, 129.0, 127.6, 122.7, 74.8, 70.6, 33.7, 29.6, 26.9, 22.6.

Example 2

The following illustrate representative pharmaceutical dosage forms, containing a compound of the invention, or a salt thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. The compound or pharmaceutically acceptable salt selected from the group consisting of:

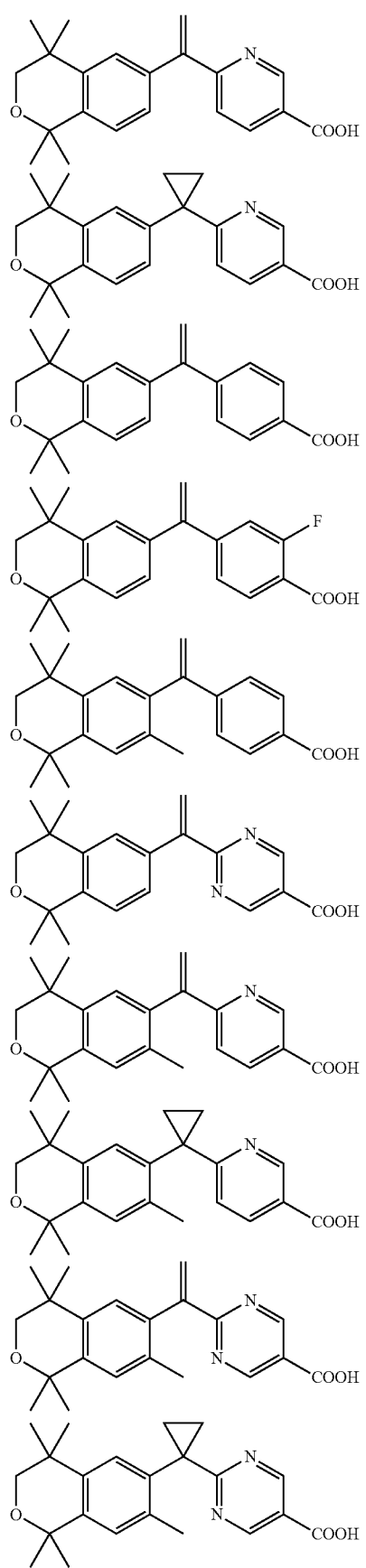
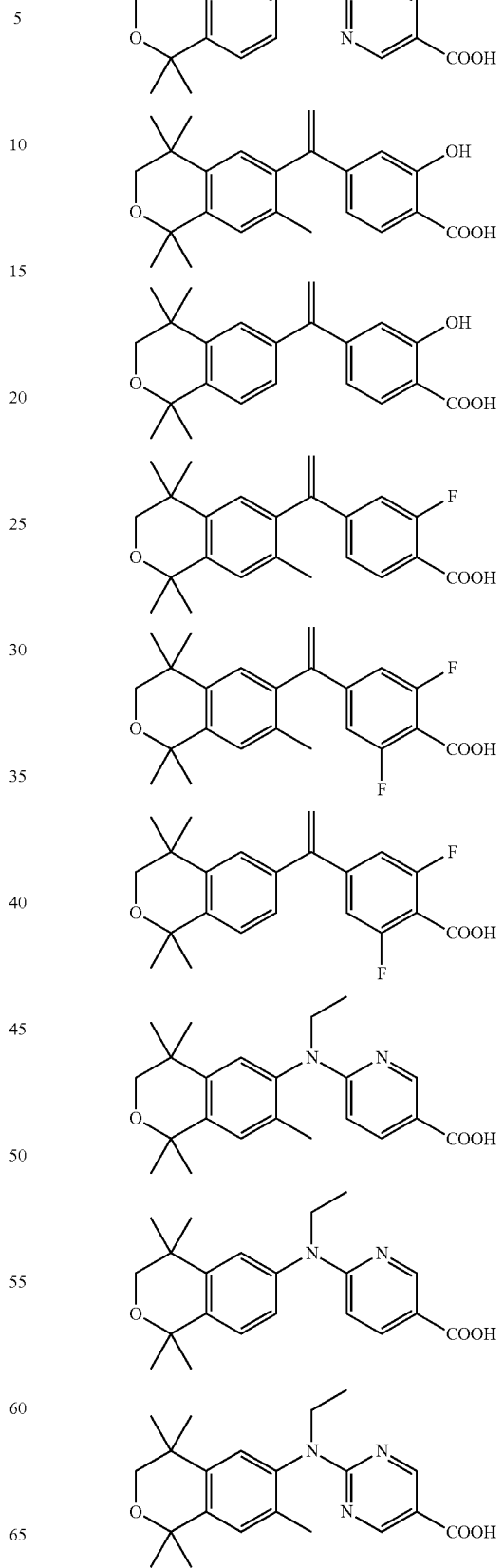

-continued

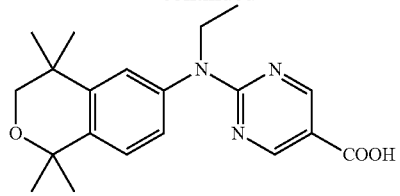

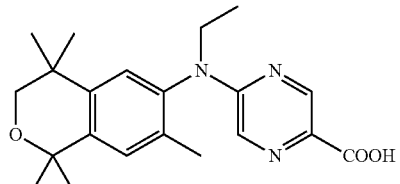

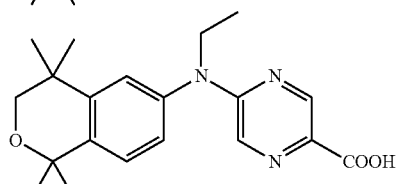

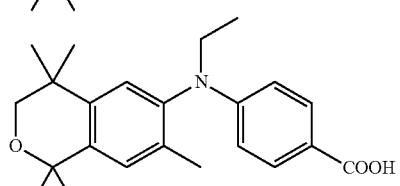

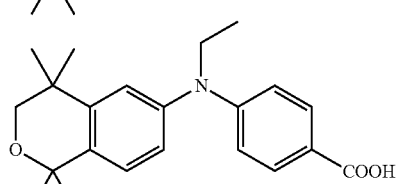

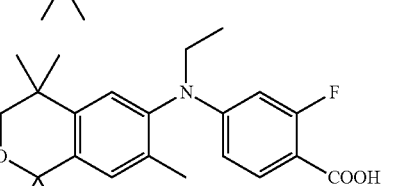

and

-continued

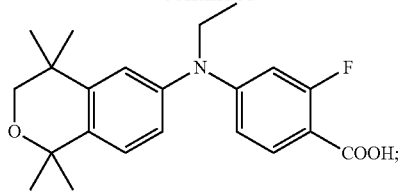

or a salt thereof.

2. A pharmaceutical composition comprising a compound as described in claim 1, or a pharmaceutically acceptable salt thereof, and a pharmaceutically acceptable diluent or carrier.

3. A method for inhibiting cancer cell growth comprising contacting the cell in vitro or in vivo with an effective amount of a compound as described in claim 1, or a salt thereof.

4. A method for treating cancer in a mammal having cancer comprising administering to the mammal an effective amount of compound as described in claim 1, or a pharmaceutically acceptable salt thereof.

5. The method of claim 4 wherein the cancer is glioblastoma multiforme, breast, lung, colon, pancreatic, skin, cutaneous T-cell lymphoma, acute promyelocytic leukemia, ovarian, bladder, kidney, head and neck cancers, or Kaposi's sarcoma.

6. A method for activating RXR in a cell comprising contacting the cell in vitro or in vivo with an effective amount of a compound as described in claim 1, or a salt thereof.

7. A method for treating Alzheimer's disease in a human having Alzheimer's disease comprising administering to the human an effective amount of compound as described in claim 1, or a pharmaceutically acceptable salt.

8. A method for treating multiple sclerosis, a disease associated with demyelination, in a mammal having multiple sclerosis comprising administering to the mammal an effective amount of compound as described in claim 1, or a pharmaceutically, acceptable salt.

* * * * *